United States Patent [19]

Scott et al.

[11] Patent Number: 5,157,339
[45] Date of Patent: Oct. 20, 1992

[54] METHOD FOR MEASURING WATER-OIL MIXTURES WITH RELATIVELY HIGH GAS CONTENT

[75] Inventors: Bentley N. Scott, Richardson; Y. Sam Yang, Dallas, both of Tex.

[73] Assignee: Atlantic Richfield Company, Los Angeles, Calif.

[21] Appl. No.: 686,065

[22] Filed: Apr. 16, 1991

[51] Int. Cl.[5] .............................................. G01N 22/00
[52] U.S. Cl. .................................... 324/640; 324/639; 73/61.43
[58] Field of Search ........ 324/629, 632, 637, 639–641, 324/643, 647; 73/61.1 R, 61 R

[56] References Cited

U.S. PATENT DOCUMENTS 4,866,370 9/1989 Flemming ........................... 324/639
4,996,490 2/1991 Scott et al. .......................... 324/639
5,025,222 6/1991 Scott et al. ...................... 324/641 X Primary Examiner—Jack B. Harvey
Attorney, Agent, or Firm—Michael E. Martin

[57] ABSTRACT

The concentration of one liquid, such as water, in another liquid, such as crude or refined oil, existing in a mixture which also includes entrained gas is carried out by an apparatus which measures a change in a microwave oscillator operating frequency and the difference between incident and transmitted power with respect to a measurement section of the apparatus. Continuous monitoring of the difference in incident versus transmitted power is carried out to detect the presence of gas and then selectively averaged peak values of the concentration of one liquid in another are determined to provide an accurate measurement of the content of water in oil even with the presence of various amounts of entrained gas in the mixture.

7 Claims, 3 Drawing Sheets

METHOD FOR MEASURING WATER-OIL MIXTURES WITH RELATIVELY HIGH GAS CONTENT

BACKGROUND OF THE INVENTION

1. Field of the Invention

The present invention pertains to a method for measuring the water or oil content of a water-oil mixture or the components of other two-phase liquid mixtures having a high concentration of entrained gas using microwave radiation measurement of frequency change and power loss through a measuring apparatus.

2. Background

U.S. Pat. No. 4,996,490, issued Feb. 26, 1991 to Scott, et al., and assigned to the assignee of the present invention describes an improved method and apparatus using microwave radiation for measuring the water content of an oil-water mixture over a relatively wide range of water content in the mixture. In measuring the content of water in crude oil, known as the watercut measurement, it has been considered necessary with prior art systems to first perform a separation process to remove as much gas from the mixture as possible. Typically, fluid flowstreams emitting from oil wells may contain a wide range of water, oil and gas in the mixture, thereby making fluid flow measurements difficult without expensive separation equipment and processes.

Although the above-described device and method provide a unique solution to so-called watercut measurement processes, it has heretofore also been considered necessary to remove as much gas from the mixture as possible before subjecting it to the microwave measurement technique. This added gas separation process at each well or elsewhere in the fluid gathering system is, of course, expensive and requires facilities which must be continuously maintained. It is highly desirable to be able to measure the amount of water in a crude oil flowstream at the wellhead or before significant separation processes are required, particularly in multi-owner oil fields where production is commingled before separation is performed.

There are, of course, other applications wherein it is desirable to know the content of one fluid in a multi-fluid mixture. The method of the present invention is believed to solve a problem heretofore unrealized, particularly in the use of microwave radiation-type measurement devices for measuring multi-component liquid mixtures.

SUMMARY OF THE INVENTION

The present invention pertains to an improved method of measuring oil-water mixtures which include relatively large amounts of entrained gases, such mixtures being typically present in the production of crude oil from underground reservoirs. In accordance with one aspect of the present invention, a system of a type described in the aforementioned U.S. patent application, the subject matter of which is incorporated herein by reference, is used to determine the water content of an oil-water mixture and wherein the water content may be determined even though a significant amount of gas may be entrained in the mixture.

Still further in accordance with the present invention, there is provided a method for measuring the water content of an oil-water mixture over a relatively wide range of amounts of water in the mixture and over a relatively wide range of amounts of gas entrained in the mixture wherein a microwave radiation transmission apparatus is utilized as the measurement device. Operating frequency and power loss of a microwave signal are measured at a significant number of measurement intervals, and the presence of gas is determined by the variation or scatter of power loss values measured. The water content of the mixture is determined for each measurement of the oil-water-gas mixture, and a statistical method is carried out for determining the true amount of water in the mixture regardless of the amount of entrained gas present.

Those skilled in the art will further recognize the advantages and superior features of the present invention upon reading the detailed description which follows in conjunction with the drawing.

DESCRIPTION OF A PREFERRED EMBODIMENT

Figure 1:
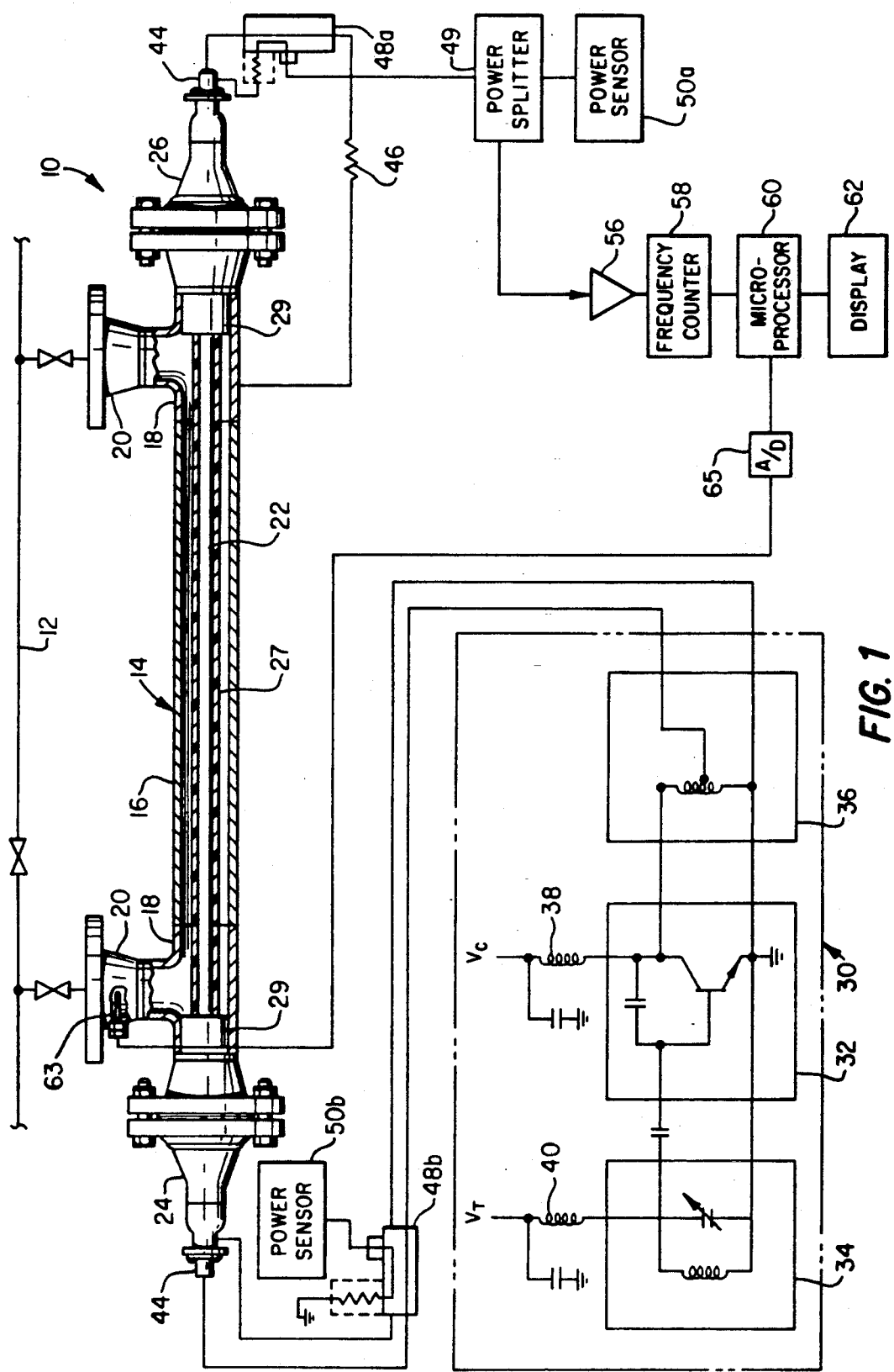
FIG. 1 is a schematic diagram of a system for measuring the water content of an oil-water mixture with or without gas entrained in the mixture.

In the description which follows, like parts or features are marked throughout the specification and drawing with the same reference numerals, respectively.

FIG. 1 illustrates an apparatus for measuring the concentration of one substance, such as water, in another substance, such as crude oil, being transmitted through a pipeline or the like, for example. The apparatus 10 is similar to that described in U.S. Pat. No. 4,996,490, which is incorporated herein by reference. The apparatus 10 includes a fluid measurement section 14 comprising an outer conduit 16 and spaced-apart pipe T-sections 18 having conventional flange portions 20 formed thereon for connection to branch conduits of a pipeline 12. The measurement section 14 includes a coaxial transmission line having a center conductor 22 extending between opposed support parts 24 and 26. The center conductor 22 preferably comprises a generally cylindrical rod or tube coaxially arranged in the conduit 16 and having an outer sheath 27 formed of a material having a relatively low dielectric loss tangent such as a plastic sold under the trademark Delrin. The insulating sheath 27 prevents radio frequency (RF) energy from being shorted out immediately at the point where RF energy enters the measurement section or where the fluid cross-section begins. The sheath 27 must be thick enough to maintain a reasonable coaxial impedance to be able to propagate RF energy into the measurement section 14 and maintain a fluid measurement capability.

The center conductor 22 extends through opposed end block members 29 formed of a relatively high insulative material such as a fluorocarbon plastic. The measurement section 14 is connected to a source of RF or so-called microwave energy comprising an unbuffered or unisolated, free-running oscillator 30. The oscillator 30 preferably includes an active circuit 32, a tuning circuit 34 and an impedance-matching network 36. The circuit 32 is adapted to receive a constant DC voltage, $V_c$, from a source, not shown, by way of a filter circuit 38. The tuning circuit is adapted to receive a controllable DC voltage, $V_t$, from another source by way of a second filter 40. The oscillator 30 has an appreciable load-pulling characteristic. One preferred type of oscillator is available from Avantek Company, Santa Clara, Calif., as their Model No. VTO8030, Voltage Control Oscillator. The oscillator 30 is connected to the measurement section 14 through a suitable connector 44 which is in electrically-conductive engagement with the center conductor 22 at the end part 24 and at the opposite end of the center conductor through a second conductor 44, a resistance 46 and with the outer conductor or conduit 16, as illustrated. The end part 26 is adapted to connect the center conductor 22 with a 10-db directional coupler 48a to sample the microwave energy or power transmitted through the measurement section 14. The coupler 48a is connected to a power splitter 49 which is connected to a power sensor 50a.

A second directional coupler 48b is interposed in the circuit between the end part 24 and the oscillator 30 and is connected to a second power sensor 50b. The coupler 48a is connected to the power splitter 49 which provides an output signal which is amplified by an amplifier 56. The amplifier 56 is adapted to provide an input signal to a frequency counter 58 which is also adapted to be connected to a microprocessor 60. A suitable digital display or readout device 62 is connected to the microprocessor 60. The system illustrated in FIG. 1 preferably includes a temperature compensation circuit, including a thermocouple 63 connected to a conversion circuit 65 to provide a suitable digital signal to the microprocessor 60.

Alternatively, the aforedescribed measurement section 14 could be provided with a short circuit in place of the support piece 26 and connector 44. Such an arrangement would provide a signal path down the measurement section which reflects off of the shorted end and returns to the oscillator end. If a dual directional coupler is substituted for the single coupler 48 and power sensors are connected to sample both the incident power and reflected power, this ratio becomes the insertion loss of the measurement section plus fluids.

Figure 2:
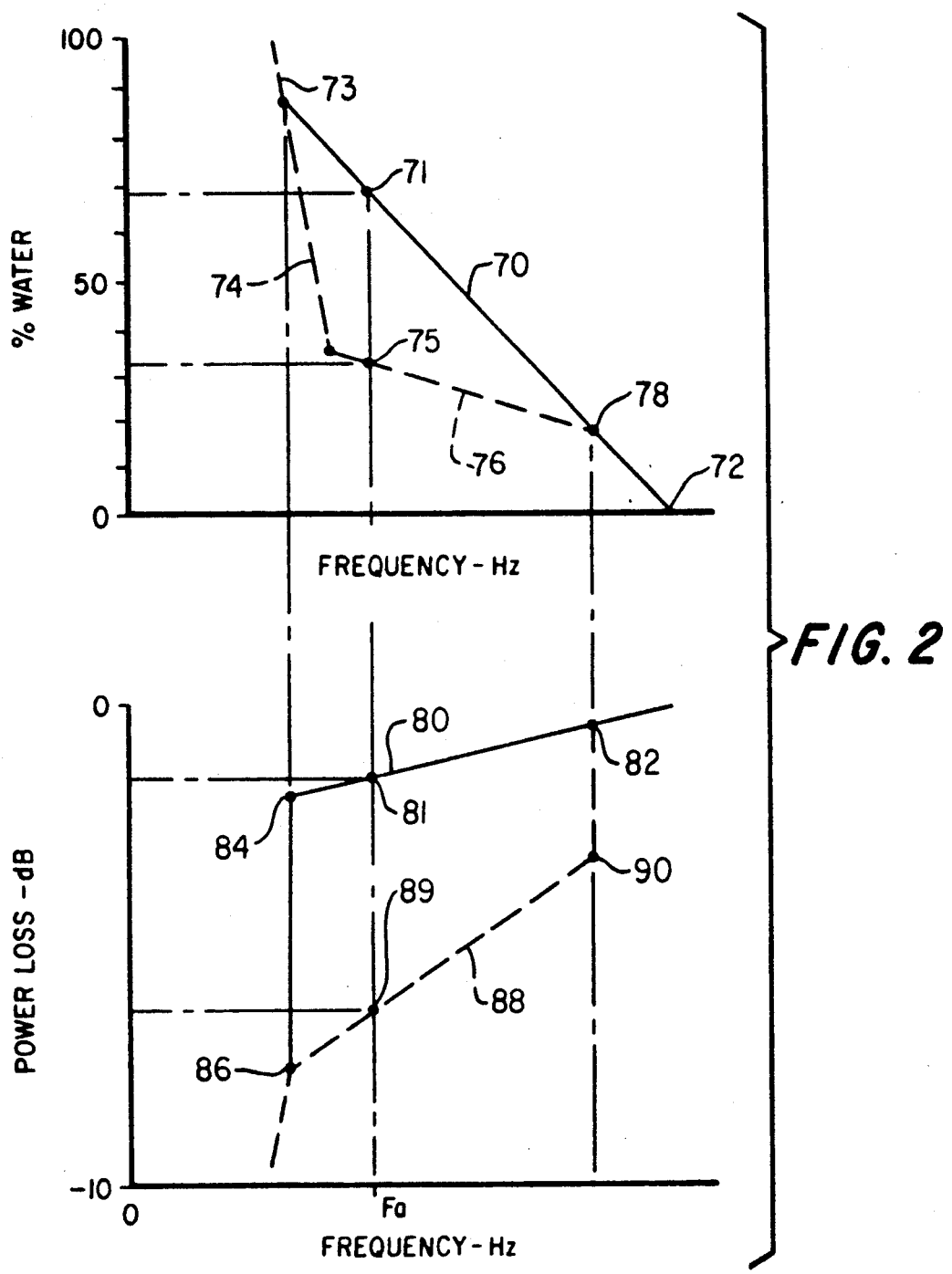
FIG. 2 is a diagram illustrating the water content and power loss of microwave radiation as a function of microwave transmission frequency.

Referring now to FIG. 2, the diagram illustrates the characteristics in the change in oscillator operating frequency as a function of the concentration of water in an oil, such as crude petroleum. The frequency of operation of the oscillator 30 as a function of the percentage of water in a water-oil mixture is indicated by the curve or line 70. As the percentage of water in a water-crude oil mixture increases to about 50% of the total volume, the water exists as an emulsion in the oil liquid. In a range of concentration of about 50% to 86% water, an inversion may occur wherein the emulsion becomes one of oil-in-water rather than water-in-oil. At above 86% water, almost universally, the emulsion is one of oil-in-water. A slight increase in the slope of curve 70 occurs over the portion 73 in the range of about 86% to 100% water.

When increasing the concentration of water in a water-oil mixture, the characteristic of the frequency change of the oscillator is indicated by the curve 70. However, in instances where a relatively high concentration of water in the mixture is initially present but then decreases, and/or wherein an oil-in-water emulsion exists, the change in oscillator operating frequency follows a curve or line 74. This dashed line follows the slope indicated in the diagram to a point wherein the amount of water equals about 36% by volume, at which point, generally, the slope of the curve changes to follow a line 76 to a point where it intersects the line 70 as indicated at point 78. It has been observed that, with changing conditions of a liquid mixture comprising water and oil, for example, a measurement of the oscillator operating frequency alone as an indication of the water content in the mixture may be unreliable since, in the range of about 20% to 86% water in the mixture, by volume, more than one operating frequency can be indicated by the apparatus 10.

As discussed in U.S. Pat. No. 4,996,490, it has been discovered that there is also a change in the microwave radiation power loss through the measurement section 14 as a function of the condition wherein there is either a water-in-oil mixture or an oil-in-water mixture. As shown in the diagram which represents frequency in the abscissa versus microwave power loss in the ordinate, the line 80 indicates the power loss through the measurement section 14 for a condition of water-in-oil from the point 82 to the point 84, 86. The line 88 in the diagram of frequency versus power loss indicates power loss for a condition where the mixture is essentially an oil-in-water emulsion.

Accordingly, during operation of the system 10, the incident power sensed at the power sensor 50b may be monitored and the transmitted power as determined by the power sensor 50a may be monitored. The difference between the readings of these power sensors is then measured to determine the power loss at a particular operating frequency of the oscillator circuit. For example, at an operating frequency of $F_a$, if the power loss corresponds to the loss indicated by the curve 88 at point 89, it is indicated that an oil-in-water mixture exists. For the same operating frequency, viewing the diagram of frequency versus percentage of water, it is indicated that approximately 30% of water is present. On the other hand, for an operating frequency of $F_a$, if the power loss corresponds to that indicated by the curve 80 at point 81, it is known that a much higher percentage of water is present in a so-called water-in-oil mixture and corresponding to the percentage indicated by the point 71 on line 70.

Figure 3:
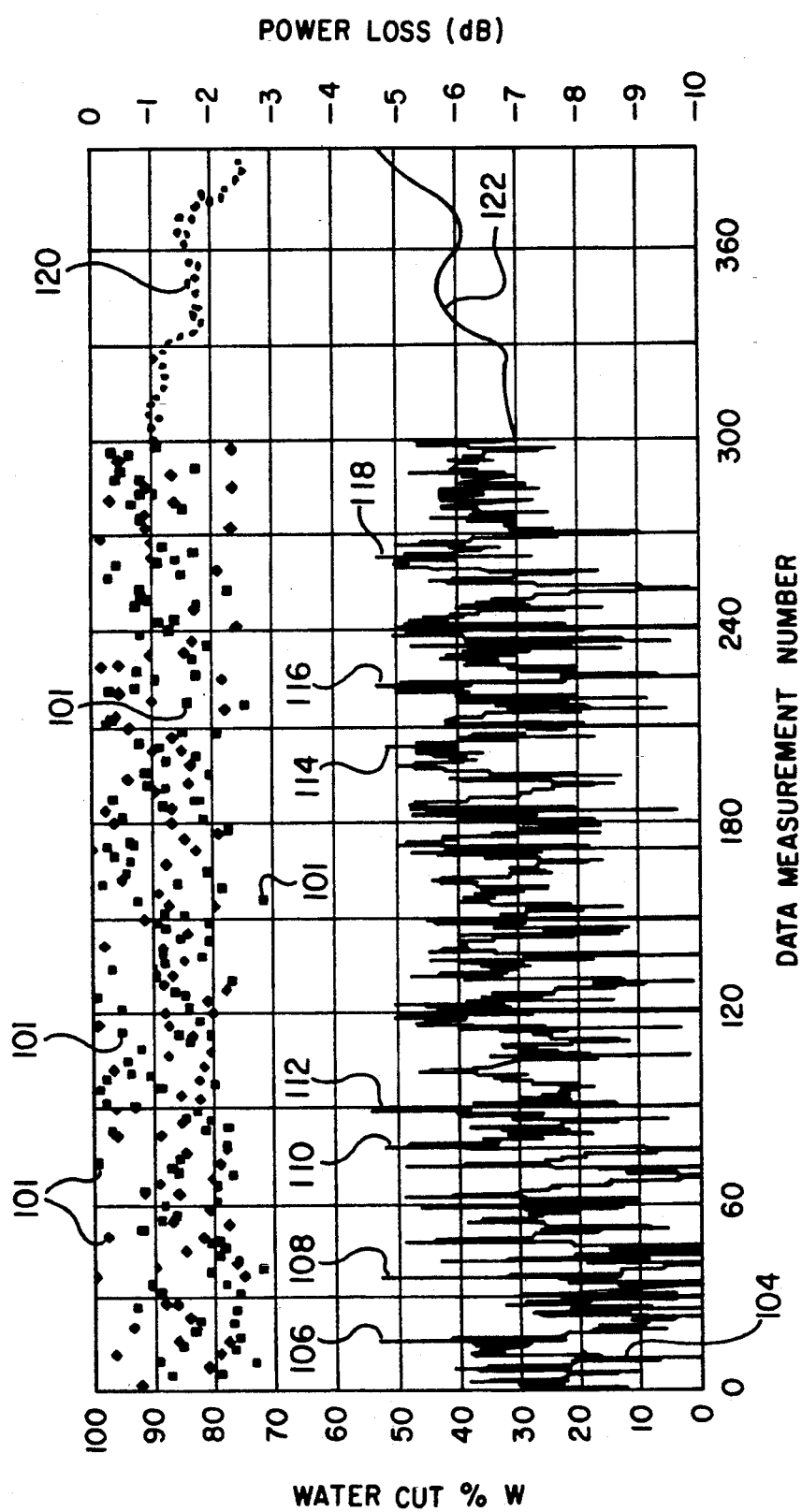
FIG. 3 is a diagram illustrating power loss and percent water content for plural measurements of an oil-water mixture containing entrained gas.

In operation of the apparatus 10 described above, under conditions wherein the water-oil mixture does not contain an appreciable amount of entrained gas (less than about three percent by volume), the power loss values form a substantially continuous curve in both the water-in-oil and oil-in-water conditions. However, when gas is present in the mixture, the power loss varies sporadically within a range of a few dB, depending on the volume fraction and the distribution of the gas in the mixture. The microwave frequency reading may become essentially uninterpretable since it varies in such a wide range based on the original calibration of the system without the presence of gas in the mixture being measured. FIG. 3, for example, indicates the power loss in dB for a substantial number of data measurement points, indicated by data measurement numbers 0 through 300, of a mixture of water, oil and gas. As indicated by the data points 101, there is a relatively wide variation in power loss over a relatively short period of time (200 milliseconds, for example) indicating that a fairly substantial amount of gas is present entrained in the liquid mixture.

All gases have a relative dielectric constant of approximately 1.00, with the third and fourth decimal place varying due to chemical composition. Gas impacts a measurement in proportion to the fluids relative dielectric constant. Therefore, a gas will affect a water measurement more than that of oil (dielectric constant of water is 68-80 and oil is 2.2-2.7). Since water produced with crude oil typically contains a high ionic salt content, the microwave loss is large. Gases exhibit very low microwave loss. The loss for oil is low in comparison to water, but gas still has a significant decreasing effect on power loss. Increasing gas content tends to decrease the calculated water content since the gas affects the dielectric like a larger volume of oil on a vol./vol. basis. More gas present increases the random-like changes of the power and frequency data. Larger "noise" appears on the power data because of the random nature of the gas flowing through the measurement section at turbulent flow rates and the dominant effect of gas decreasing the power loss. This variation in power loss alone is useful as an indication that the mixture includes entrained gas.

Referring further to FIG. 3, it is indicated that using the apparatus illustrated in FIG. 1 and the technique for determining the percent water content in accordance with the procedure of FIG. 2 and as described in U.S. Pat. No. 4,996,490, a percentage of water content may be ascertained for each data measurement point such as any one of the points 0 through 300 indicated in FIG. 3. If a percentage water content is determined for each measurement point of frequency and power loss, a plot of percent water content may be determined according to the jagged line 104 indicated in FIG. 3. If only those values of water content indicated by the peak values such as the values 106, 108, 110, 112, 114, 116 and 118, for example, are considered, then it has been determined from tests that an accurate measurement of the percent water content may be obtained by taking a running average of the peak values of water content as indicated by the data points 106 through 118.

For example, by selecting only the data points which indicate a water content value in excess of 50%, as indicated by the points 106 through 118, a statistical method for determining the water content based on these values over a certain threshold may be carried out to obtain an accurate measurement of the actual water content of the mixture even though a substantial amount of gas is present. During a test of production from an oil well wherein the fluid being conducted from the well included water, oil and entrained gas, measurements of the water content w of fluid samples with gas removed varied from measurements using the data points 106 through 118, averaged, by an amount which was negligible.

One statistical method which may be used is the so-called running or moving average technique. The simplest of these techniques is that of iterated averages. For example, a first operation may be carried out by obtaining an average of four peak values of water content wherein:

$$\text{Wave} = \frac{W_{106} + W_{108} + W_{110} + W_{112}}{4}$$

Three more averages of successive sets of four peak values may be determined and then the four averages are averaged to give a value of percent water content based on the number of points taken in the diagram of FIG. 3 wherein:

$$W = \frac{\text{Wave}_1 + \text{Wave}_2 + \text{Wave}_3 + \text{Wave}_4}{4}$$

or $$W = 1/16 \ (W_{106} + 2W_{108} + 3W_{110} + 4W_{112} + 3W_{114} + 2W_{116} + W_{118})$$

These operations may, of course, be carried out automatically to provide a percent water content for measurements taken over a period of time wherein, from viewing the scattering of power loss values, it is indicated that gas is present in the liquid mixture.

By comparison, the data points shown for power loss and watercut from measurement points 301 through 390 indicate relatively smooth continuous curves 120 and 122, respectively, and are indicative of conditions wherein negligible gas is present in the fluid mixture. The water content is varying, however, as shown by the changing value indicated for "watercut" or percent water content of the liquid mixture.

From the foregoing, it is indicated that a microwave-type meter for measuring the water content of a water-oil mixture, or the content of one liquid in a two-liquid mixture which is subject to entrained gas, may be accurately determined even though gas is present in the mixture. Of course, whether or not gas is eventually separated from the mixture, the content of one liquid in the mixture is accurately determined and the results advantageously used, such as when determining net oil production from producing oil wells and the like which also produce water and entrained gas.

Although a preferred embodiment of the invention has been described hereinabove, those skilled in the art will recognize that various substitutions and modifications may be made without departing from the scope and spirit of the invention as recited in the appended claims.

What is claimed is:

1. A method of measuring the content of one liquid in a mixture of at least two liquids wherein said mixture includes entrained gas and using the alteration of microwave energy characteristics, said method comprising the steps:

providing apparatus including means forming a measurement section having means for transmitting microwave radiation therethrough, means operably connected to said means for transmitting microwave radiation at an operating frequency which changes, means for measuring a change in said operating frequency and means for measuring the incident power to said measurement section and the transmitted power through said measurement section to determine the power loss of microwave radiation in said measurement section;

operating said apparatus and making measurements of changes in the operating frequency due to changes in the composition of the mixture flowing through said measurement section;

determining the power loss of microwave radiation in said measurement section at selected operating frequencies;

making a predetermined number of said measurements while observing the change in operating frequency and power loss to detect the presence of gas in said liquid mixture by observing a variation in the power loss between measurement points;

determining the content of one liquid in another at each measurement of power loss by comparing the power loss at an operating frequency with a referenced power loss for a known condition of content of one liquid in another at said operating frequency; and comparing a selected number of peak values of content of one liquid in another at a selected number of measurement points to determine the actual content of one liquid in the other based on said selected number of peak values.

2. The method set forth in claim 1 wherein said liquid mixture includes a water-oil mixture and the step of measuring the power loss includes comparing the power loss to a reference power loss exhibited by a water-in-oil emulsion and a reference power loss exhibited by an oil-in-water emulsion at a particular operating frequency to determine the concentration of at least one of said water and oil in said mixture.

3. The method set forth in claim 1 including the step of:

selecting a predetermined number of peak values of content of one liquid in another based on said measurements and performing a statistical analysis of said selected sets of measurements to obtain a final value of said content of one liquid in another.

4. The method set forth in claim 3 wherein:

said peak values are averaged by determining plural averages of a first set of peak values of the content of one liquid in another followed by averaging said plural averages.

5. A method of measuring the content of water liquid in a mixture of oil and water wherein said mixture includes entrained gas and using the alteration of microwave energy characteristics, said method comprising the steps:

providing apparatus including means forming a measurement section having means for transmitting microwave radiation therethrough, means operably connected to said means for transmitting microwave radiation at an operating frequency which changes, means for measuring a change in said operating frequency and means for measuring the incident power to said measurement section and the transmitted power through said measurement section to determine the power loss of microwave radiation in said measurement section;

operating said apparatus and making measurements of changes in the operating frequency due to changes in the composition of the mixture flowing through said measurement section;

determining the power loss of microwave radiation in said measurement section at selected operating frequencies;

making a predetermined number of said measurements while observing the change in operating frequency and power loss to detect the presence of gas in said liquid mixture by observing a variation in the power loss between measurement points;

determining the content of one liquid in another at each measurement of power loss by comparing the power loss at an operating frequency with a referenced power loss for a known condition of content of one liquid in another at said operating frequency; and comparing a selected number of peak values of content of water in said mixture at a selected number of measurement points to determine the actual content of water based on said selected number of peak values.

6. The method set forth in claim 5 wherein:

said peak values are averaged by determining plural averages of a first set of peak values of the content of water in said mixture followed by averaging said plural averages.

7. A method of measuring the content of water in a mixture of at least oil and water wherein said mixture includes entrained gas and using the alteration of microwave energy characteristics, said method comprising the steps:

providing apparatus including means forming a measurement section having means for transmitting microwave radiation therethrough, means operably connected to said means for transmitting microwave radiation at an operating frequency which changes, means for measuring a change in said operating frequency and means for measuring the incident power to said measurement section and the transmitted power through said measurement section to determine the power loss of microwave radiation in said measurement section;

operating said apparatus and making measurements of changes in the operating frequency due to changes in the composition of the mixture flowing through said measurement section;

measuring the power loss of microwave radiation in said measurement section at selected operating frequencies;

comparing the measured power loss to a reference power loss exhibited by a water-in-oil emulsion and a reference power loss exhibited by an oil-in-water emulsion at a particular operating frequency.

making a predetermined number of said measurements while observing the change in operating frequency and power loss to detect the presence of gas in said liquid mixture by observing a variation in the power loss between measurement points;

determining the content of water in said mixture at each measurement of power loss by comparing the power loss at an operating frequency with a referenced power loss for a known condition of content of water in said mixture at said operating frequency; and comparing a selected number of peak values of content of water in said mixture at a selected number of measurement points to determine the actual content of water in said mixture based on said selected number of peak values.

* * * * *